United States Patent
Yankielun et al.

[19]

[11] Patent Number: 6,121,894
[45] Date of Patent: Sep. 19, 2000

[54] LOW COST TIME DOMAIN REFLECTOMETRY SYSTEM FOR BRIDGE SCOUR DETECTION AND MONITORING

[75] Inventors: Norbert E. Yankielun, Lebanon, N.H.; Leonard Zabilansky, Perkinsville, Vt.

[73] Assignee: U.S. Army Corps of Engineers as represented by the Secretary of the Army, Washington, D.C.

[21] Appl. No.: 09/197,438

[22] Filed: Nov. 23, 1998

[51] Int. Cl.⁷ .................................................. G08C 19/06
[52] U.S. Cl. ...................................... 340/870.31; 367/131
[58] Field of Search ...................... 340/870.31; 367/131, 367/13; 405/73

[56] References Cited

U.S. PATENT DOCUMENTS

| | | |
|---|---|---|
| 2,707,267 | 4/1955 | Gavin . |
| 3,617,996 | 11/1971 | Herbert . |
| 3,727,128 | 4/1973 | McFerrin . |
| 3,991,364 | 11/1976 | Wiznerowicz . |
| 4,855,966 | 8/1989 | Cinquino . |
| 4,914,394 | 4/1990 | Meyer . |
| 5,361,776 | 11/1994 | Samuelson et al. . |
| 5,479,724 | 1/1996 | Nahajski et al. . |
| 5,532,687 | 7/1996 | Richardson et al. . |
| 5,554,936 | 9/1996 | Mohr . |
| 5,784,338 | 7/1998 | Yankielun et al. ................. 367/131 |

*Primary Examiner*—Michael Horabik
*Assistant Examiner*—Timothy Edwards, Jr.
*Attorney, Agent, or Firm*—Luther A. Marsh

[57] ABSTRACT

An apparatus for detecting and monitoring scouring around a structural member uses time-domain reflectometry (TDR) to measure the level of sediment around a submerged portion of the structural member such as a bridge pier, dock, utility crossing, or similar structure. The apparatus includes a time domain reflectometer which transmits a series of electrical pulses, a sensor which is connected with said time-domain reflectometer, and a signal analyzer which receives and interprets the portion of the electrical pulses reflected back to the source from an interface, such as water/air or water/gravel, to calculate the position of the interface along the sensor. Knowledge of the position of the interfaces before and after a scouring event and of the dielectric constant of the surrounding media allows the user to detect and monitor the level of erosion caused by scouring.

12 Claims, 2 Drawing Sheets

LOW COST TIME DOMAIN REFLECTOMETRY SYSTEM FOR BRIDGE SCOUR DETECTION AND MONITORING

BACKGROUND OF THE INVENTION

The present invention relates to a bridge scour detection and monitoring apparatus and, more particularly, to a low cost time domain reflectometry (TDR) system for real-time detection and monitoring of sediment levels around the submerged foundation of a structural member such as a bridge.

Bridge scour is a severe problem that costs millions of dollars in terms of damage, loss of life, and required annual maintenance by leaving infrastructure, including bridge piers and docks, in unsafe conditions. A scouring event occurs during times of rapid river flow and icing conditions when sediment, including rocks, gravel, and silt is transported by river currents away from bridge piers and similar structures. Scour is dynamic, and ablation and deposition can occur during the same high-energy flow event, so the net effect cannot be easily predicted. If the event is severe enough, foundation material below the pier footing may erode, leaving the structure unsupported and in jeopardy of collapse. Measurement of scour is therefore useful in monitoring stability and repair needs for bridges and other waterway structures before major damage occurs.

BRIEF DESCRIPTION OF THE RELATED ART

Currently, there are several techniques and devices used for detecting and monitoring scour, including subsurface interface radar, transducers, optical fathometers, physical probes, and visual inspection. All of these devices suffer from significant drawbacks.

Radar has been successfully employed to bathymetrically determine scour conditions. The technique is usually used after an event, indicating the final status of the sedimentation surrounding a pier. Sonar techniques have been similarly employed. Neither of these techniques are continuously employed in situ during a scour event and both require skilled operators to perform the test and interpret the results.

Neutral buoyancy sensors or "fish" equipped with a seismic transducer and a radio transmitter have been anchored at varying depths in the sediment around bridge piers (Zabilansky, L. J., *Ice Force and Scour Instrumentation for the White River*, Cold Regions Research and Engineering Laboratory, Hanover, N.H., Special Report 96-6, April 1996). As the fish are uncovered by the scouring process they are moved by the currents and they transmit signals to a receiver located on the shore to indicate that the scour has reached their tethered depth. When the sediment is redeposited, the fish are then re-buried at approximately their original depth. While this system is resettable, it still provides a fairly crude spatial indication of the scour progression. Also, the fish are battery powered and thus have a limited life and must be replaced periodically.

Various devices are known in the patented prior art for detecting and monitoring scouring. The U.S. Pat. No. 4,502,044 to Cinquino, for example, discloses a method and apparatus for monitoring bridge structures for scouring having apparatus for determining the distance between the topmost portion of the soil bed and one or more fixed points on a pier. In one embodiment of the invention, the distance determining apparatus comprises a sonar device for determining the distance between the soil bed and a fixed point on the pier.

The U.S. Pat. No. 3,617,996 to Herbert discloses an apparatus for scour detection at bridge piers and the like utilizing a plurality of electroacoustical transducers mounted on the structure to measure the effects of scouring on the soil bed adjacent to the structure.

Scouring measurement and detection utilizing time domain reflectometry (TDR) has been suggested in the literature (Dowding, C. H. and Pierce, C. E., *Use of Time Domain Reflectometry to Detect Bridge Scour and Monitor Pier Movement*, United States Department of Interior Bureau of Mines, Symposium and Workshop of Time Domain Reflectometry in Environmental, Infrastructure and Mining Applications, Northwestern University, Illinois, Sep. 7–9, 1994). However, such systems differ from the present invention in that they employ a sacrificial sensor buried vertically in the sediment. Once a section of the sensor is exposed by scouring, the current causes the exposed section to be broken off, therefore shortening the sensor. This shortening of the sensor can then be detected and measured by an off-shore instrument. The drawback to this technique is that the sacrificial sensor, which is destroyed in the measurement process, must be replaced after every event. Also, these systems utilize expensive electronic TDR equipment to perform the measurements.

The present invention was developed in order to overcome these and other drawbacks of the prior devices by providing a bridge scour detection and monitoring device which takes advantage of a low cost time domain reflectometry (TDR) circuit design for real-time measurement of sediment levels around a submerged structural member. The principle of TDR is widely known and applied to numerous measuring and testing applications. TDR operates by generating an electromagnetic pulse (or a fast rise time step) and coupling it to a transmission line. The pulse propagates down the transmission line at a fixed and calculable velocity which is a function of the speed of light in addition to the electrical and physical characteristics of the transmission line. The pulse will propagate down the transmission line until it reaches the end of the line where it will be reflected back towards the source. The time t in seconds that it takes for the pulse to propagate down and back the length of the transmission line is called the "round trip travel time" and is calculated as:

$$t = 2L/v$$

where:
  L = length of a parallel metal rod sensor (m)
  v = velocity of propagation (m/s)
The velocity of propagation can be given as:

$$v = c/(E^{1/2}) = c/n$$

where:
  c = velocity of light in free space ($3 \times 10^8$ m/s)
  E = the relative dielectric constant of the media surrounding the transmission line
  n = index of refraction of the media surrounding the transmission line.

In the case of a two wire parallel transmission line, changes in the dielectric media in the immediate surrounding volume will cause a change in the round trip travel time. Freshwater has a dielectric constant E of 80, ice has a dielectric constant of 3.17, and dry sedimentary materials (e.g.: soil, gravel and stone) have dielectric constants in the range of 5 to 8. Wet sediment has a dielectric constant which is a mixture of those of water and dry soil. The dielectric constant E of this mixture will vary depending upon the local sedimentary material constituency, but in all cases the bulk dielectric (bulk index of refraction) of the mixture will be less than that of water alone and significantly greater than that of the dry sedimentary materials.

At any interface along the transmission line such as at an air/water interface or a water/sediment interface, a dielectric discontinuity exists. As a pulse traveling down the transmission line encounters the air/water interface, a portion of the pulse energy is reflected back to the source by the interface while the remaining portion of the energy will continue to propagate through the interface until the pulse encounters another interface or the end of the transmission line where part or all of the remaining pulse energy is reflected back along the transmission line to the source.

The series of reflected pulses form a signature signal which a signal analyzer unit interprets to calculate the position of the interfaces along the transmission line as a function of the time elapsing between the reflected pulses and dielectric constants of the surrounding media. Knowledge of the positions of the interfaces over a period of time allows the user to detect and monitor the level of erosion caused by scouring.

SUMMARY OF THE INVENTION

Accordingly, a primary object of the present invention is to provide a real-time bridge scour detection and monitoring system which uses a low cost time-domain reflectometry (TDR) circuit design to measure the level of sediment around the submerged portion of a structural member such as a bridge, pier, dock, utility crossing, or the like. The apparatus includes a time domain reflectometer for transmitting a series of electromagnetic pulses and electrical step signals having a square wave generator for generating an electrical signal, a fast rise-time generator connected with the square wave generator for receiving the electrical signal and producing a fast rise-time electrical step signal, and a high pass filter for converting the series of fast rise-time electrical step signals into electromagnetic pulses. Connected with the time domain reflectometer is a sensor for receiving and reflecting fast rise-time electrical step signals as a function of the surrounding media, and a signal analyzer which receives and interprets the electrical pulses from the time domain reflectometer to determine the position of an interface, such as water/air or water/gravel.

It is another object of the invention to provide a bridge scouring detection and monitoring system that is built with a relatively inexpensive time domain reflectometer circuit design and uses a robust permanent sensor arrangement which may be economically and easily deployed.

It is another object of the invention to provide a bridge scour detection and monitoring system with a comparator to compare an initial reference set of interface positions with a subsequently measured set of positions to trigger an alarm when a significant change is observed in the TDR signature or when a difference in the position of the interfaces over time exceeds a predetermined threshold.

It is a further object of the invention to provide a bridge scour detection and monitoring system having minimal user interface, simple installation, and low maintenance due in part to the fact that the system has no moving or mechanical components.

BRIEF DESCRIPTION OF THE DRAWINGS

Other object and advantages of the invention will become apparent from a study of the following specification when viewed in light of the accompanying drawings, in which.

DETAILED DESCRIPTION

Figure 1:
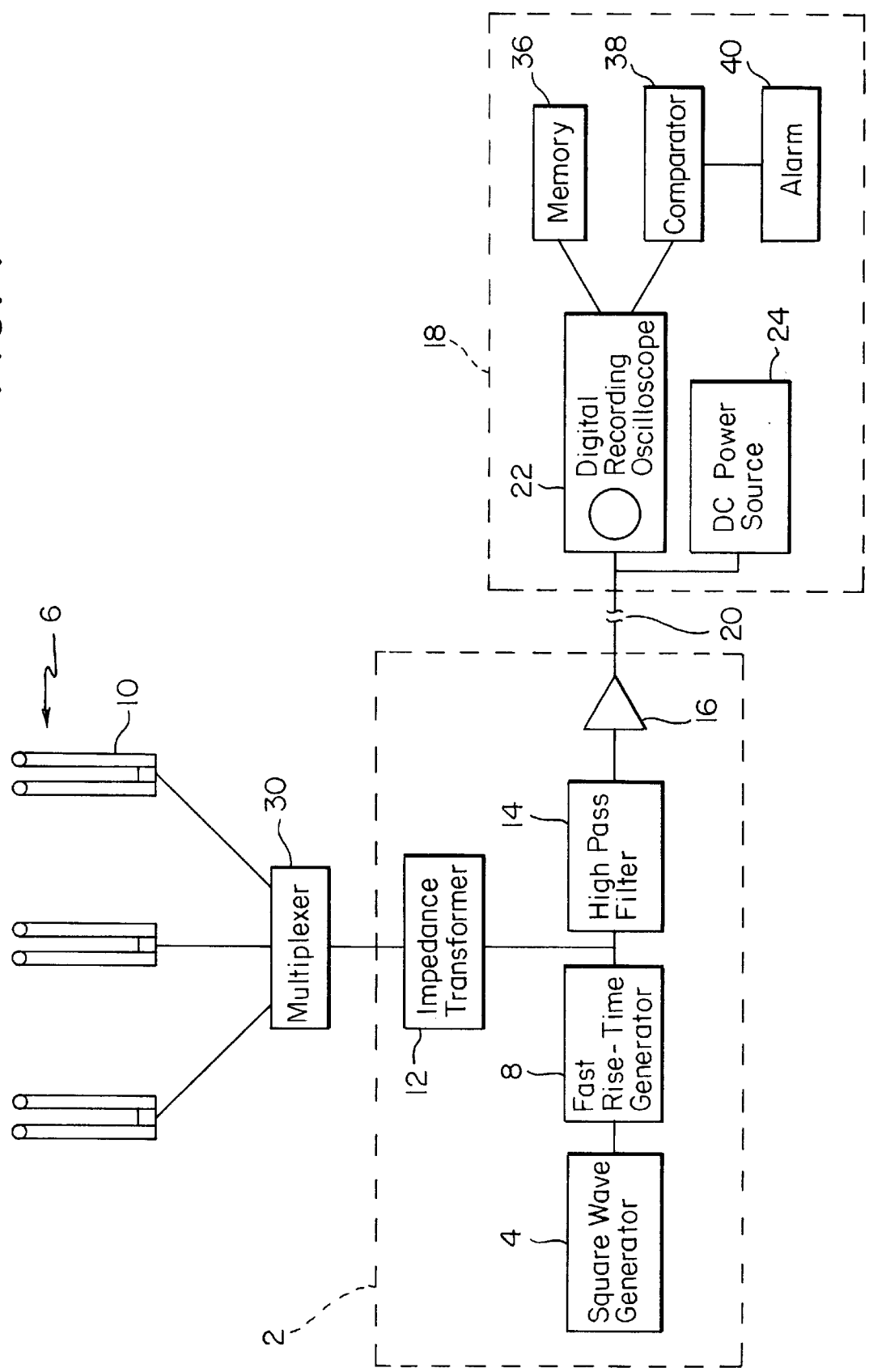
FIG. 1 is a schematic view of scour monitoring apparatus including a time domain reflectometer and signal analyzer according to the invention.

Referring now to FIG. 1, there is shown a time domain reflectometer 2 having a square wave generator 4 which generates an electrical signal with a period that is significantly longer than the round-trip travel time of an electrical signal propagating on the sensor rods 6. A square wave with a 1 ms period is significantly long for this application, although shorter or longer square waves would work as well as long as they meet the previous condition.

Connected with the square wave generator 4 is a fast rise-time generator 8. The fast rise-time generator 8 is triggered by reception of the relatively slow rise-time electrical signal of the square wave generator 4 to generate an electrical signal with an acceptably sharp rise-time. This is necessary since the typical square wave generator 4 does not have a suitable steep rise-time to be effective for time domain reflectometry measurements.

Typical time domain reflectometry systems generate a 200 ps to a 20 ns rise-time step. The rise-time (slope) of the transition from one level to another of the signal (typically ground or zero volts to a known constant voltage level) applied to the sensor determines the minimal spatial resolution of the time domain reflectometer. A slower or less steep rise-time relates to a lower spatial resolution. Therefore, as described above, to produce an electrical signal with an acceptably sharp rise-time, the square wave generator 4 is used to trigger a fast rise-time generator 8.

Sensors 6 are connected with the fast rise-time generator 8 for coupling the fast rise-time electrical signal of the fast generator 8 with the sensor 6. Sensor 6 is arranged within the sedimentation bed and is adapted for receiving and reflecting fast rise-time step signals. The reflected fast rise-time signals are a time-domain function of the properties of the surrounding media through which the sensor 6 passes. Preferably, the sensor 6 comprises a pair of parallel transmission rods 10 which are electrically coupled with the fast rise-time generator 8.

To minimize the energy reflection of the fast rise-time generator 8 to sensor 6 interconnection, and thus permit a greater portion of the signal energy to propagate along the sensor 6, it is necessary to match the impedance of the fast rise-time generator 8 closely to that of the sensor 6. Impedance matching can be accomplished either by using an impedance transformer 12 or designing the physical dimensions of the sensor 6 to insure an impedance match. Although this impedance will change as the dielectric media (water or water/sediment mix) surrounding the sensor 6 changes, this is not expected to significantly affect the ability of the probe to clearly delineate the interface boundaries necessary to calculate scour depth.

Also connected with the fast rise-time generator 8 is a high pass filter 14 which acts as a differentiator. The high pass filter 14 converts the fast rise-time steps generated by the fast rise-time generator 8 and those reflected from the sensor 6 into electromagnetic pulses. With the high pass filter 14 installed, the time domain reflectometer circuit performs as a pulse-TDR. Without the high pass filter 14, the TDR circuit performs as a step-TDR. Each has advantages, depending on the specific application and interface between the time domain reflectometer 2 and the signal analyzer 18.

Additionally, an amplifier 16 can be added at the output of the high pass filter 14 if needed to increase the output signal to an acceptable level for transmission to the signal analyzer 18.

The signal analyzer 18 is remotely connected with the time domain reflectometer 2 via a cable 20, and is capable of receiving and analyzing electromagnetic pulses, whereby changes between the pulses and in the elapsed propagation time thereof can be determined as a measure of the scour resulting from shifting of sediment and other material in the floor of the body of water. The signal analyzer 18 includes a digital recording oscilloscope 22 connected with the cable 20 for displaying the electromagnetic pulses. Additionally, there is a DC power source 24, preferably a battery, connected with the cable 20 for supplying power to the TDR 2.

Figure 2:
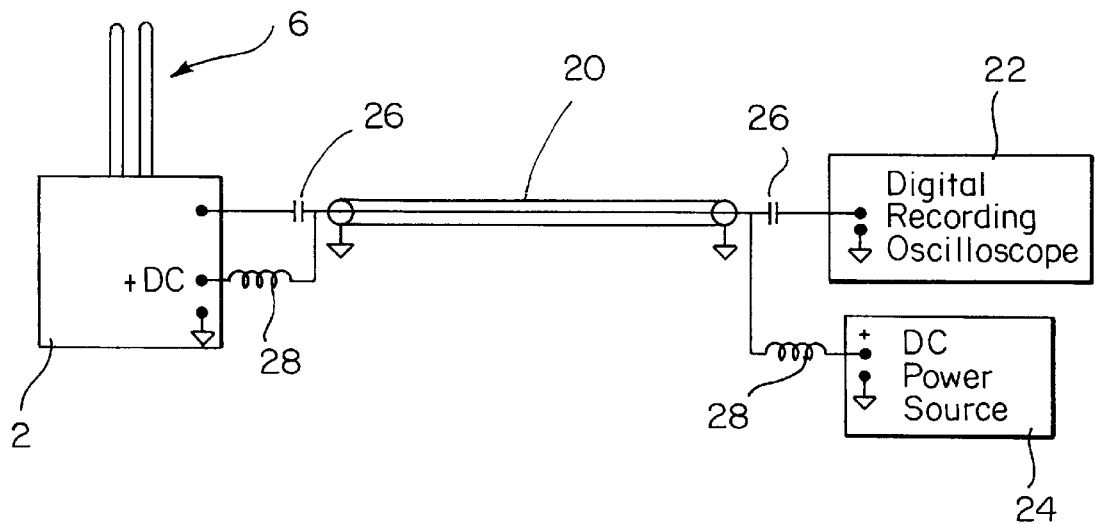
FIG. 2 is a schematic view of a circuit design to enable a single coaxial cable to provide both an AC and a DC signal simultaneously.

Cable 20 may consist of single or multiple cables. However, FIG. 2 illustrates a method of using a single coaxial cable 20 to provide a time domain reflectometer 2 with DC power while simultaneously providing a path for the TDR signal to the digital recording oscilloscope 22. As shown, the TDR signal is coupled from the time domain reflectometer 2 to the oscilloscope 22 through the coaxial cable 20. Two capacitors 26, one at each end of the cable 20, act to block direct current while permitting passage of the TDR signal via a low impedance AC path. Similarly, two inductors 28, one at each end of the cable 20, provide a low impedance DC path, to permit direct current to flow from the battery 24 to power the TDR circuitry while inhibiting the flow of the TDR signal from that path. Both the signal and power circuits use the coaxial shield 30 of the cable 20 as a common ground conductor.

Figure 3:
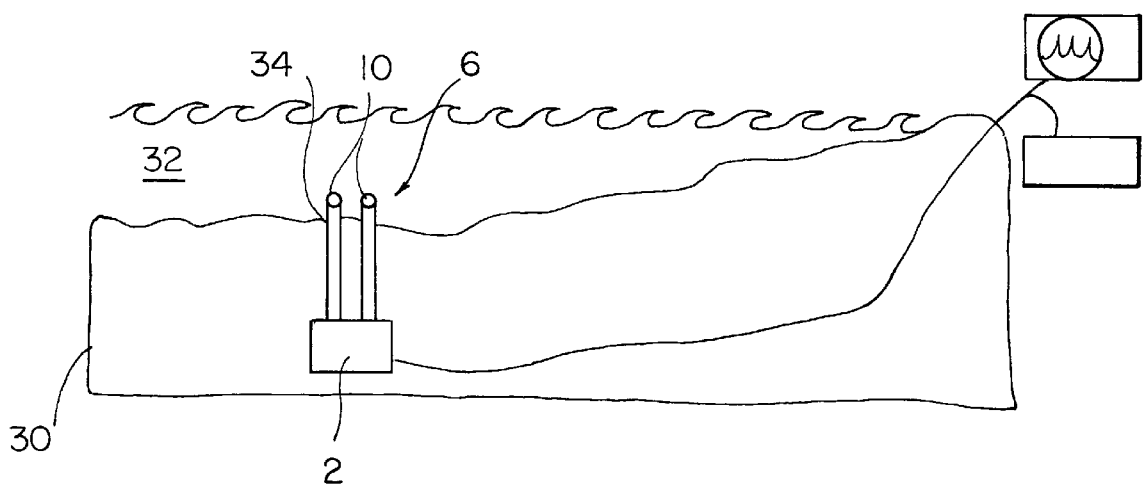
FIG. 3 is a schematic view illustrating the placement of a coaxial cable and sensor within the sediment of a body of water.

FIG. 3 illustrates an installed time domain reflectometer 2 and sensor 6 unit strategically positioned vertically within a sediment layer 30 beneath a body of water 32 at a depth which would permit anchoring of the device in the sediment 30 below the expected limit of maximum scouring activity. As scouring occurs and the sediment 30 erodes, the transmission lines 10 are exposed to the surrounding water 32 which causes an interface 34 to form along the transmission lines 10. The position of the developing interface 34 along the transmission lines 10 can be measured to determine the progression of scouring. A later scouring event may result in a favorable reshifting of sediment 30 that will rebury the transmission lines 10 where they will rest until the next scouring event. The sensors 6 can also be strategically placed in various arrays enabling three-dimensional mapping of the effects of scouring within the sediment 30.

Following installation of the system at a particular area of concern, an initial reference measurement of the interface position 34 along each sensor 6 is taken by propagating an electrical step signal along the transmission lines 10. This initial reading is transmitted to the remotely located signal analyzer 18 where it is stored in a memory 36 included in the signal analyzer 18. Subsequent measurements of sets of interface positions 34 are frequently taken and stored in a memory 36 to record the position of sediment levels as a result of scouring over time. The signal analyzer 18 also includes a comparator 38 to calculate the change over time and the measurement of the interface position 34 between the initial reference set of interface positions and a subsequently measured set of interface positions. The comparator 38 can use a real time computer algorithm to compare multiple measurements of interface positions 34 and may also trigger an alarm 40 when a significant change is observed or when a predetermined threshold difference between measurements of interface positions is exceeded.

An alternative embodiment of the invention is shown in FIG. 1 wherein a multiplexer 42 is interconnected between the time domain reflectometer 2 and a plurality of transmission rods 10. In this configuration, pairs of parallel transmission lines 10 are positioned at areas of interest within the sediment floor and the multiplexer 42 automatically and electrically multiplexes the numerous pairs of parallel transmission lines 10 into a single time domain reflectometer 2 and signal analyzer 18.

The system can also be configured so that the time domain reflectometer 2 instrument is detachably connected to the parallel transmission lines 10 so that they may be periodically, i.e., monthly, transported to a structural site and manually interfaced to each of the transmission lines 10. By sharing the time domain reflectometer instrument 2 among numerous infrastructure sites, further economy of operation can be gained.

While in accordance with the provisions of the Patent Statutes the preferred forms and embodiments of the invention have been illustrated and described, it will be apparent to those of ordinary skill in the art that various changes and modifications may be made without deviating from the inventive concepts set forth above.

What is claimed is:

1. Apparatus for monitoring scouring around a structural member having a lower portion submerged beneath the sediment floor of a body of water, comprising
   (a) time domain reflectometer means for generating a plurality of electromagnetic pulses and electrical step signals, including:
      (1) a square wave generator for generating an electrical signal having a rise-time;
      (2) a fast rise-time generator connected with said square wave generator for receiving said electrical signal from said square wave generator and producing said electrical step signal having a fast rise-time relative to that of said square wave generator; and
      (3) a high pass filter connected with said fast rise-time generator for converting a fast rise-time electrical signal into said electromagnetic pulses;
   (b) sensor means for receiving and reflecting said electrical step signals connected with said pulse generator means and arranged within the sediment of the body of water, said sensor means comprising at least one pair of parallel transmission lines which receive and reflect said fast rise-time step signals, said reflected signals being a time-domain function of the properties of the surrounding media through which said sensor means passes; and
   (c) signal analyzer means connected with said time domain reflectometer means for receiving and analyzing said electromagnetic pulses, whereby changes between said electromagnetic pulses and in the elapsed propagation times thereof can be determined as a measure of the scouring at the structural member resulting from shifting of sediment and other material in the floor of the body of water.

2. Apparatus as defined in claim 1, wherein said time domain reflectometer means further includes an impedance transformer interconnected between said time domain reflectometer means and said sensor means for matching the impedance of said time domain reflectometer means to that of said sensor means, thereby permitting a greater portion of said fast rise-time step signal to propagate along the sensor.

3. Apparatus as defined in claim 1, wherein said signal analyzer means is a recording digital oscilloscope for displaying said electromagnetic pulses.

4. Apparatus as defined in claim 3, wherein said signal analyzer means includes a power source for supplying DC power to said time domain reflectometer means.

5. Apparatus as defined in claim 1, and further comprising a coaxial transmission line connecting said pulse generator means with said signal analyzer, said coaxial transmission line having a pair of capacitors connected in series with said line to provide a low impedance AC path and a pair of inductors connected in series with said line to provide a low impedance DC path, whereby transmission of both of said DC power supply and said AC electromagnetic pulses is simultaneously accomplished over said single coaxial transmission line.

6. Apparatus as defined in claim 1, wherein said reflected pulses are a time-domain function of the relative dielectric constants of the surrounding media through which said sensor means passes.

7. Apparatus as defined in claim 1, wherein said pulse generator means further includes amplification means for increasing the signal strength transmitted from the pulse generator means to the signal analyzer means.

8. Apparatus as defined in claim 1, wherein said sensor means comprises a plurality of pairs of parallel transmission lines, and further comprising multiplexing means connected between said sensor means and said pulse generator and signal analyzer means for monitoring said plurality of said pairs of parallel transmission lines with one of said pulse generating means and said signal analyzing means.

9. Apparatus as defined in claim 1, wherein said signal analyzer means includes a memory means for storing a plurality of measurements of scouring adjacent the structural member.

10. Apparatus as defined in claim 9, wherein said signal analyzer means further includes comparator means for calculating a change over time between said stored measurements of scouring adjacent the structural member.

11. Apparatus as defined in claim 10, wherein said comparator means calculates said change over time in said stored measurements of scouring between an initial reference measurement and a subsequent measurement of scouring adjacent the structural member.

12. Apparatus as defined in claim 10, wherein said signal analyzing means further includes an alarm, said alarm being triggered if said change over time between said stored measurements of scouring is greater than a predetermined threshold.

\* \* \* \* \*